United States Patent [19]

Bertholet et al.

[11] Patent Number: 4,722,923
[45] Date of Patent: Feb. 2, 1988

[54] DOUBLE SULFATE SALT OF DESOXYFRUCTOSYL SEROTONIN AND CREATININE AND COMPOSITIONS CONTAINING IT

[75] Inventors: Raymond Bertholet, Blonay; Pierre Hirsbrunner, Les Monts-de-Corsier, both of Switzerland

[73] Assignee: Nestec S.A., Vevey, Switzerland

[21] Appl. No.: 756,052

[22] Filed: Jul. 17, 1985

[30] Foreign Application Priority Data

Aug. 9, 1984 [CH] Switzerland .................. 3823/84

[51] Int. Cl.$^4$ .................. A61K 31/70; C07H 7/06
[52] U.S. Cl. .................. 514/23; 536/55
[58] Field of Search .................. 536/55; 514/23

[56] References Cited

FOREIGN PATENT DOCUMENTS 2317937 3/1978 France .
1551141 8/1979 United Kingdom .

OTHER PUBLICATIONS

J. E. Hodge, et al., "Amadori Rearrangement Products", Methods in Carbohydrate Chemistry, vol. II, 1963, pp. 99–107.
Chemical Abstracts, vol. 94, 1981, p. 102, 94:41940r.
P. Jayaraman, et al., "Inhibition of the Incorporation of [$^3$H]DOPA in Mycobacterium Leprae by Desoxyfructoserotonin", Biochemical Pharmacology, vol. 29, 1980, pp. 2526–2528.
WIPO Publication No. WO84/04310 (8, Nov. 1984).

*Primary Examiner*—Nicky Chan
*Attorney, Agent, or Firm*—Vogt & O'Donnell

[57] ABSTRACT

A double sulfate salt of 1-desoxy-(5-hydroxytryptamino)-D-fructose (DSF) and 1-methylhydantoin-2-imide (creatinine) represents a new solid crystalline phase of unit composition, pharmaceutical quality and remarkable stability.

It is prepared by glycosylation of serotonin with D-glucose, formation of the double salt by addition of sulfuric acid and creatinine and crystallization of the double salt in the presence of ethanol.

The DFS is preferably isolated from the reaction medium by way of the addition complex DFS.Ca(OH)$_2$ which is precipitated by the addition of calcium hydroxide. The calcium hydroxide is then eliminated by addition of sulfuric acid and the double salt is crystallized as described above.

DFS is the active principle of a medicament effective, in particular, in the treatment of leprosy.

13 Claims, No Drawings

DOUBLE SULFATE SALT OF DESOXYFRUCTOSYL SEROTONIN AND CREATININE AND COMPOSITIONS CONTAINING IT

This invention relates to a double sulfate salt of desoxyfructosyl serotonin and creatinine, to a process for the production thereof and to a medicament containing this compound.

French Pat. No. 2,317,937 relates to new derivatives of serotonin (5-hydroxytryptamine), more especially the oxalate of 1-desoxy-(5-hydroxytryptamino)-D-fructose or desoxyfructosyl serotonin, hereinafter referred to as "DFS", obtained by Amadori rearrangement. In this French Patent, DFS is described as a medicament effective against platelet agglutination and in affording protection against radiation. More recently, DFS has proved to be extremely active in the treatment of leprosy (Jayaraman P., Mahadevan P. R., Mester L., Mester M., Biochemical Pharmacology, Vol. 29, 2526-8, 1980).

It is known that, if the active substance in question is to be used as a medicament, it must be presented in a crystalline and stable unit form. However, DFS is unstable: it is in the form of a white, amorphous and non-crystallizable product which turns brown after about 1 day at ambient temperature, forming polymers. The oxalate of DFS is also amorphous, yellow in color, contains impurities and turns brown in storage which rules out its use as a medicament. Because of its high solubility in water, the oxalate has proved impossible to obtain in solid form by standard crystallization techniques using solvents, for example alcohol, the application of low temperatures, the addition of seed crystals, etc.

The present invention relates to a double sulfate salt of 1-desoxy-5-hydroxytryptamino)-D-fructose and 1-methylhydantoin-2-imide (creatinine) in crystalline form which does not have any of the disadvantages of the described compounds.

This salt is soluble in aqueous media at low temperatures and highly soluble therein at high temperatures. Since a 1 by weight aqueous solution has a pH value of 3.5, the secondary amine and imine functions, respectively, of DFS and 1-methylhydantoin-2-imide are protonated, enabling the following formula to be attributed to the salt:

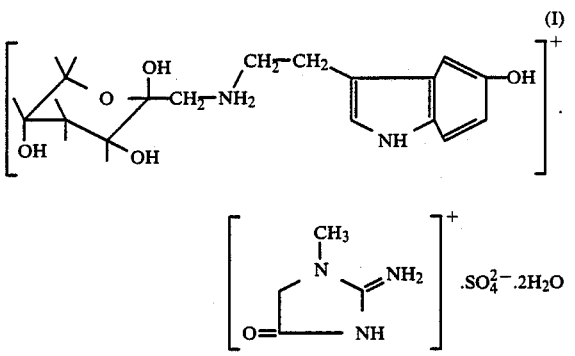

hereinafter referred to in short as "DFSCS".

A study using a polarizing optical microscope has shown that this new solid phase, which is in the form of a white crystalline powder, is composed of highly birefringent, low symmetry crystals of the monoclinic or triclinic type.

Chemical analysis has enabled the composition of the crystals to be established, leading, by application of the law of single proportions, to a double sulfate.

With a molecular weight of 585.6 and a melting range of 136°-140° C. (with decomposition), DFSCS has an apparent density of approximately 30 g/100 ml and a rotatory power $[\alpha]$ 20/ D of $-20.0°$ to $-21.0°$ (c=1, water).

It is insoluble in alcohols containing 2 and more carbon atoms, ethers, esters, ketones and halogenated solvents, slightly soluble in methanol and soluble in dimethyl sulfoxide.

It is characterized by remarkabe stability in the solid phase. After storage for 6 months at 45° C. in the form of capsules in a glass container, no change was observed.

The present invention also relates to a process for the production of DFSCS, characterized in that 1-methylhydantoin-2-imide is added to an aqueous solution of DFS containing sulfuric acid at a pH of approximately 3 and in that the DFSCS is separated from the reaction medium.

Separation is preferably carried out by concentration of the aqueous solution, addition of a water-miscible solvent, in which the DFSCS is insoluble, and crystallization of the DFSCS.

It is preferred to use a slight excess of creatinine in relation to the DFS, for example of from 1.1 to 1.2 times the molar quantity of DFS. The solution may be concentrated to approximately half its volume, for example, by evaporation under reduced pressure.

Acetone or $C_1$–$C_4$ alcohols, preferably ethanol, are advantageously used as the solvent.

The crystals formed are then separated, for example by filtration, and dried, for example, in vacuo. After optional recrystallization, for example, from water/ethanol, filtration and drying as indicated above, the DFSCS is collected in the form of white crystals.

The DFS used as starting product may be obtained, for example, by condensation of D-glucose with 5-hydroxytryptamine, followed by Amadori rearrangement (conversion of the N-glycoside of an aldose into the N-glycoside of the corresponding ketose in the presence of an acidic or basic catalyst) using known methods (cf., "Methods in Carbohydrate Chemistry", Vol. 2, Academic Press N.Y., 1963, page 99).

It is preferred to use an excess of D-glucose of from 1.5 to 3 times the molar quantity of serotonin present. The serotonin is advantageously present in the form of one of its salts, for example, the hydrogenoacetate.

The reaction is carried out in an anhydrous solvent in an inert atmosphere, for example, in a nitrogen atmosphere, in order to avoid hydrolysis of the intermediate aldosylamine. The solvent should be able to solubilize the glucose and the serotonin. It is of advantage to use a lower alcohol, i.e., an alcohol containing from 1 to 4 carbon atoms, for example, methanol, ethanol or isopropanol, methanol being preferred because it provides for better selectivity of the reaction.

The reaction is preferably catalyzed by acids. The acid used as catalyst is selected from mineral or, preferably, organic acids which, depending on their type and the quantity in which they are added, enable a pH of from 3 to 5 and, preferabaly pH of 4.2 to be adjusted in the reaction medium. Acids suitable for use as catalysts include mono- or polycarboxylic acids, for example, formic acid, oxalic acid or acetic acid, formic acid being preferred.

The reaction temperature ranges from ambient temperature to the reflux temperature of the solvent.

The reaction generally lasts 30 to 150 minutes. Depending on its duration, the reaction is more or less complete and gives a mixture containing, based on the weight of the serotonin-containing species, from 60 to 83% of DFS, from 3 to 35% of residual serotonin and from 5 to 14% of secondary products. The excess glucose and the acid introduced are also found in the reaction medium.

Water is preferably added to the reaction medium and the solvent eliminated, for example, by distillation under reduced pressure. The aqueous solution is advantageously decolored, for example, with active carbon, and sulfuric acid, preferably concentrated, is added in the quantity necessary to adjust the solution to a pH of approximately 3.

Both the DFS, hydrolyzable to serotonin, and the serotonin itself may be recycled, but not the secondary products, i.e., the di- and tri-substituted derivatives and the polymers.

In one preferred variant, the reaction is interrupted after approximately 40 minutes and, after the DFSCS has been separated as described above, the serotonin is extracted from the liquid phase by ion exchange or, preferably, with a solvent. In this latter case, for example, the pH of the liquid phase is adjusted to the isoelectric point of the serotonin by addition of a strong base, for example, sodium or potassium hydroxide, i.e., to approximately 10.8, after which the serotonin is extracted with an aliphatic alcohol containing from 4 to 8 carbon atoms, for example, isobutanol or a benzyl alcohol (i.e., benzyl or methylbenzyl alcohol) and, after elimination of the solvent, the serotonin is recycled upstream of the reaction by which the DFS is formed. Advantageously, the serotonin to be recycled is converted into the form of the salt which was used for the reaction. The alcohol, for example, isobutanol, solution is thus neutralized to a pH of approximately 6, for example, with acetic acid, and the solvent is eliminated, for example, by evaporation under reduced pressure.

In one preferred embodiment of the process according to the invention for preparing the aqueous solution of DFS containing sulfuric acid, an excess of calcium hydroxide over the DFS is added to the reaction medium containing the DFS in the presence of water, an insoluble addition complex is collected and treated with an acid which precipitates calcium, the calcium is eliminated in the form of an insoluble salt, the DFS in solution is collected and sulfuric acid is added to the solution.

By adding calcium hydroxide, preferably in the form of an aqueous or aqueous-alcoholic suspension, with stirring at ambient temperature in a molar ratio of DFS to $Ca(OH)_2$ of 35 from 1:3 to 1:4, an addition complex of the "sucrate" type is formed. A reducing agent, for example, sodium dithionite, is preferably also added to the suspension. After about 10 minutes, the solid phase is filtered and washed with water.

The serotonin present in the mother liquors is advantageously recovered. To this end, sulfuric acid is added until the solution has a pH of approximately 3, the calcium sulfate formed is eliminated, for example, by filtration, most of the water is eliminated, for example, by evaporation under reduced pressure, and, after the pH of the solution has been adjusted to approximately 10.8, the serotonin is extracted with an aliphatic alcohol containing from 4 to 8 carbon atoms or with a benzyl alcohol and then converted into the desired salt as described in the foregoing.

The insoluble complex $DFS.Ca(OH)_2$, constituting the solid phase mentioned above, is then suspended in water. The pH of the suspension is highly alkaline, i.e., from 12 to 13.

The calcium is precipitated in the form of a salt by treating the addition complex in aqueous suspension with a suitable acid. The choice of the acid is dictated by its ability to form, with the calcium, a salt which is insoluble in the aqueous media. The acid used may be an organic or mineral acid, for example, oxalic acid, citric acid, tartaric acid or phosphoric acid or, preferably, sulfuric acid, preferably concentrated. The insoluble calcium salts corresponding to the acids used, for example, $CaSO_4.2H_2O$ (gypsum) in the case of sulfuric acid, are precipitated.

Separation of the solid phase, for example, by filtration, leaves, for example, the oxalate, citrate, tartrate or even the hydrogenophosphate or, preferably, the neutral sulfate of DFS in solution.

In one preferred embodiment of the process according to the invention, in which the neutral sulfate of DFS is prepared in solution, a slight molar excess of creatinine and sulfuric acid are added to the solution as described above and the DFSCS is obtained by crystallization with alcohol.

After the solid phase has been dried and optionally recrystallized, for example, from a mixture of alcohol and water, the salt obtained contains approximately 90% of the theoretical quantity of DFS. Based on the serotonin used, the yield is of the order of 60%.

Calcium hydroxide is preferably added to the mother liquors, from which the alcohol has been eliminated by evaporation, the insoluble complex is separated, for example, by filtration, and recycled to the calcium hydroxide addition stage by incorporation in the following batch. Recycling of the $DFS.Ca(OH)_2$ complex enables the yield to be increased to approximately 70%.

By recovering the serotonin from the mother liquors after precipitation of the $DFS.Ca(OH)_2$ complex, the yield is increased to approximately 80%. By comparison, according to French Pat. No. 2 317 937, the crude oxalate of DFS is obtained in amorphous form in a yield of approximately 25%.

The present invention also relates to a medicament containing DFSCS as active principle.

The medicament according to the invention is formulated according to the mode of administration.

If administered, for example, in unit dosage form by the oral or enteral route, the medicament may be formulated as a syrup, capsules, gelatin capsules, tablets or dragees.

For administration by the parenteral route, for example, the medicament may be formulated as a sterile and apyrogenic, physically and chemically stabilized solution or suspension.

For topical administration for example, the medicament may be formulated as a lotion, ointment, milk, cream or gel.

The concentration of the active principle may be from 10 to 50% by weight.

For example, a daily dose of from 400 to 450 mg taken in the form of gelatin capsules is suitable for the treatment of leprosy.

The invention is illustrated by the following Examples in which the percentages and parts are by weight, unless otherwise indicated.

EXAMPLE 1

2.36 g of serotonin hydrogenoacetate (10 mmoles), 3.6 g of anhydrous D-glucose (20 mmoles), 0.65 g of formic acid and 75 ml of anhydrous methanol are heated under nitrogen for 150 minutes to reflux temperature (60° C.). 50 ml of water are added and the methanol is eliminated by distillation in vacuo. The aqueous solution is decolored with 1.5 g of active carbon. After filtration, 0.9 g of creatinine (8 mmoles) and 2.8 g of 30% sulfuric acid are added to adjust the pH-value to 3, followed by concentration. 33 g of an orange-colored solution are thus obtained. After the gradual addition of 75 ml of 96% ethanol, a crystalline phase appears, being separated by filtration and then washed with 96% ethanol. After drying in vacuo at 40° C., 2.45 g of pale beige colored crystals are obtained. After recrystallization from water/ethanol, filtration and drying, white crystals corresponding to formula I above are collected in a yield of 2.12 g.

The structure was verified by proton and carbon NMR spectroscopy and by chemical analysis:

|  | Analysis (% by weight) | Theoretical (% by weight) |
| --- | --- | --- |
| Total nitrogen | 12.12 | 11.97 |
| $H_2O$ (K. Fischer method) | 6.48 | 6.15 |
| Creatinine | 19.8 | 19.32 |
| $H_2SO_4$ (acidimetric method, METROHM ® titration curve) | 16.75 | 17.05 |

EXAMPLE 2

To 600 g of methanol are added 23.6 g of serotonin hydrogenoacetate (0.1 mole), 27.0 g of anhydrous D-glucose and 6.5 g of formic acid. This mixture is heated for 20 minutes in an inert atmosphere to reflux temperature. After this treatment, all the serotonin has reacted to form 25 g of DFS plus secondary products. 300 g of water are added to the reaction mixture after which the methanol is distilled in vacuo. 2.5 g of sodium dithionite and 30 g of calcium hydroxide (suspended in 50 g of water) are added to the acidic (pH 3.9) aqueous solution obtained. A solid phase appears. The mixture (pH 12.2) is stirred for 10 minutes and then filtered. The solid phase collected, which consists of the complex $DFS.Ca(OH)_2$ and an excess of $Ca(OH)_2$, is washed with water. The impurities and the salts are present in the filtrate.

The solid phase obtained as described above is suspended in 250 g of water. 95 g of 30% sulfuric acid are added, followed by stirring for 60 minutes. This treatment releases the DFS from its complex and precipitates the calcium in the form of gypsum ($CaSO_4.2H_2O$) which is separated by filtration. The filtrate (pH 6) containing the DFS in the form of its neutral sulfate is decolored while stirring with 5 g of active carbon. After filtration, 400 g of an orange-colored solution are obtained. 9.0 g of creatinine (0.08 mole) and 17 g of 30% sulfuric acid are then added to adjust the pH of this solution to 3. This solution of DFSCS is concentrated in vacuo to a weight of 170 g, after which 360 g of 96% ethanol are slowly added with stirring. A crystalline phase appears and, after stirr'ng for 1 hour at ambient temperature, the crystals formed are filtered, washed with 150 g of 85% ethanol and then dried in vacuo at 40° C. 37.0 g of pale beige crystals are thus collected.

The mother liquor of crystallization is concentrated and the residual aqueous phase, which still contains 6.5 g of DFS, is treated in the same way as before. This requires 6 g of $Ca(OH)_2$ and then 17 g of 30% sulfuric acid. After concentration of the filtrate and addition of 2 g of creatinine, crystallization at pH 3 gives another 5.0 g of pale beige crystals.

The total obtained amounts to 42.0 g. This product has a DFS content of 52.5%. Recrystallization from water/ethanol gives 37.1 g of white crystals containing 55.4% of DFS and 20.8% of creatinine.

The yield of DFS is 20.5 g which corresponds to 60.6%, based on the serotonin used.

Analyses confirm the formula shown above.

EXAMPLE 3

The procedure is as in Example 2, except that the refluxing time is reduced to 40 minutes. At this stage of the reaction, only 80% of the seromonin used has reacted to form 27 g of DFS and impurities. Treatment with calcium hydroxide enables the DFS to be separated from the unreacted serotonin, the serotonin remaining soluble in the filtrate and being capable of being extrtracted.

To this end, the filtrate is concentrated in vacuo to a volume of 150 ml and then acidified to pH 3 with 30% sulfuric acid. The calcium sulfate formed ($CaSO_4.2H_2O$) is separated by filtration. The pH of the filtrate, in which the serotonin is present, is adjusted to 10.8 (isoelectric point of serotonin) by the addition of sodium hydroxide, after which the serotonin is extracted with 3×100 ml of 3 isobutanol. After elimination of the aqueous phase, the isobutanol extracts are combined, neutralized to pH 6 with acetic acid and then concentrated in vacuo. 4.0 g of serotonin hydrogenoacetate are thus collected, corresponding to 16.6% of the serotonin used.

After the various treatments described in Example 2, the solid phase (the $DFS.Ca(OH)_2$ complex) gives 45 g of white crystals containing 52% of DFS. The yield of DFS amounts to 69%. By recycling the serotonin, the yield is increased to 81%.

What is claimed is:

1. A crystalline 1-desoxy-(5-hydroxytryptamino)-D-fructose and 1-methylhydantoin-2-imide double sulfate salt.
2. A composition comprising a medicament formulation of a crystalline double sulfate salt of 1-desoxy-(5-hydroxytryptamino)-D-fructose and 1-methylhydantoin-2-imide.
3. A composition according to claim 2 wherein the formulation is in unit dosage form.
4. A composition according to claim 2 or 3 wherein the salt comprises from 10% to 50% by weight of the formulation.
5. A composition according to claim 2 wherein the formulation is in a form selected from the group consisting of tables, dragees and capsules.
6. A composition according to claim 2 wherein the formulation is in a form of a syrup.
7. A composition according to claim 2 wherein the formulation is in a form selected from the group consisting of a solution and suspension.

8. A composition according tro claim 2 wherein the formulation is in a form selected from the group consisting of a lotion, ointment, milk, cream and gel.

9. A double sulfate salt having the formula:

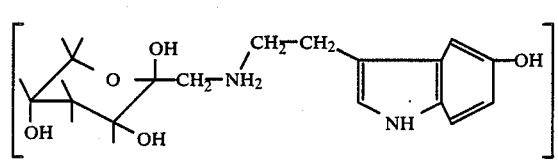

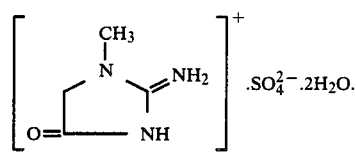

10. A method for treating leprosy comprising administering an effective amount of a crystalline double sulfate salt of 1-desoxy-(5-hydroxytryptamino)-D-fructose and 1-methylhydantoin-2-imide.

11. A method of treatment according to claim 10 wherein the salt is administered in a manner selected from the group consisting of oral, enternal, parenteral and topical administration.

12. A method of treatment according to claim 10 wherein the effective amount of the salt is a daily dose of from 400 mg to 450 mg.

13. A method of treatment according to claim 12 wherein the salt is administered in gelatin capsules.

* * * * *

UNITED STATES PATENT AND TRADEMARK OFFICE
CERTIFICATE OF CORRECTION

PATENT NO. : 4,722,923            Page 1 of 2

DATED : February 2, 1988

INVENTOR(S) : Raymond Bertholet, et al.

It is certified that error appears in the above-identified patent and that said Letters Patent is hereby corrected as shown below:

At column 1, line 38, "1-desoxy-5-hydroxytryptamino)-D-fructose" should read -- 1-desoxy-(5-hydroxytryptamino)-D-fructose --.

At column 1, line 44, after "1" insert -- % --.

At column 2, line 15, "remarkabe" should read -- remarkable --.

At column 2, line 66, "preferabaly" should read -- preferably --; a comma should appear after "preferably".

At column 3, line 57, delete "35".

At column 5, line 41, "20 minutes" should read -- 120 minutes --.

At column 5, line 68, "stirr'ng" should read -- stirring --.

UNITED STATES PATENT AND TRADEMARK OFFICE
CERTIFICATE OF CORRECTION

PATENT NO. : 4,722,923         Page 2 of 2

DATED : February 2, 1988

INVENTOR(S) : Raymond Bertholet, et al.

It is certified that error appears in the above-identified patent and that said Letters Patent is hereby corrected as shown below:

At column 6, line 28, "extrtracted" should read -- extracted --.

At column 6, line 36, delete the second occurrence of "3".

At column 6, line 37, before "isobutanol" insert -- 3 --.

At column 6, line 63, that is in line 3 of claim 5, "tables" should read -- tablets --.

At column 7, line 1, that is in line 1 of claim 8, "tro" should read -- to --.

Signed and Sealed this

Twelfth Day of July, 1988

Attest:

DONALD J. QUIGG

*Attesting Officer*      *Commissioner of Patents and Trademarks*